US008337204B2

(12) United States Patent
Lowder et al.

(10) Patent No.: US 8,337,204 B2
(45) Date of Patent: Dec. 25, 2012

(54) ROTARY DENTAL TOOL AND METHOD OF MANUFACTURE

(75) Inventors: James T. Lowder, Columbus, OH (US); Mitchell W. Haller, Jr., York, PA (US); Alan R. Lipp, Westerville, OH (US)

(73) Assignee: Spectrum Systems, LLC, Columbus, OH (US)

( * ) Notice: Subject to any disclaimer, the term of this patent is extended or adjusted under 35 U.S.C. 154(b) by 0 days.

(21) Appl. No.: 11/235,451

(22) Filed: Sep. 26, 2005

(65) Prior Publication Data

US 2006/0068358 A1    Mar. 30, 2006

Related U.S. Application Data

(60) Provisional application No. 60/613,000, filed on Sep. 24, 2004.

(51) Int. Cl.
*A61C 3/06* (2006.01)

(52) U.S. Cl. ......................................................... 433/166

(58) Field of Classification Search .................. 433/166, 433/165, 142, 125, 215; 228/122.1, 262.51; 51/295

See application file for complete search history.

(56) References Cited

U.S. PATENT DOCUMENTS

| | | | |
|---|---|---|---|
| 2,562,587 A * | 7/1951 | Swearingen | 433/166 |
| 3,762,895 A * | 10/1973 | Keeleric | 51/309 |
| 3,894,673 A * | 7/1975 | Lowder et al. | 228/124.5 |
| 4,018,576 A | 4/1977 | Lowder et al. | |
| 4,466,795 A * | 8/1984 | Plischka | 433/166 |
| 4,661,064 A * | 4/1987 | Beltramini | 433/166 |
| 4,684,346 A * | 8/1987 | Martin | 433/166 |
| 4,738,621 A | 4/1988 | Lowder | |
| 4,830,615 A * | 5/1989 | Goldstein et al. | 433/166 |
| 4,834,655 A * | 5/1989 | Kyotani | 433/166 |
| 4,883,500 A * | 11/1989 | Deakins et al. | 51/298 |
| 5,094,839 A | 3/1992 | Lowder et al. | |
| 5,211,560 A | 5/1993 | Lowder et al. | |
| 5,344,551 A * | 9/1994 | Tsai et al. | 205/110 |
| 5,492,771 A | 2/1996 | Lowder et al. | |
| 5,509,803 A * | 4/1996 | Gwilliam et al. | 433/166 |
| 5,511,718 A | 4/1996 | Lowder et al. | |
| 5,882,201 A * | 3/1999 | Salem | 433/216 |
| 6,267,595 B1 * | 7/2001 | Gratz | 433/165 |
| 6,368,107 B2 * | 4/2002 | Danger et al. | 433/166 |
| 6,565,356 B2 * | 5/2003 | Oyamada et al. | 433/166 |
| 6,676,410 B2 * | 1/2004 | Beppu | 433/166 |
| 6,780,013 B2 * | 8/2004 | Kubein-Meesenburg et al. | 433/166 |
| 2002/0037490 A1 * | 3/2002 | Oyamada et al. | 433/165 |

OTHER PUBLICATIONS

Premier Dental Products, Co., "Two Striper" sales brochure #8621254-ADS2951M.

* cited by examiner

*Primary Examiner* — Sunil K Singh
(74) *Attorney, Agent, or Firm* — James R. Eley; Michael A. Forhan; Eley Law Firm Co. LPA

(57) ABSTRACT

A rotary dental tool. The tool includes a blank having a shaft portion and a head portion. A single layer of diamond crystals extends from the blank at substantially uniform height, the diamond crystals covering a predetermined proportion of the surface area of the head portion. A bonding material substantially surrounds the diamond crystals, forming micro-channels between the diamond crystals. The diamond crystal size is substantially less than other rapid cutting tools yet out performs other tools in cutting speed, durability and smoothness of finish. The micro-channels are believed to both cool the dental tool and facilitate debris removal during use.

20 Claims, 6 Drawing Sheets

ROTARY DENTAL TOOL AND METHOD OF MANUFACTURE

This application claims priority to U.S. provisional patent application 60/613,000, filed Sep. 24, 2004, the contents of which are hereby incorporated by reference.

FIELD

This invention relates generally to rotary diamond dental instruments and, more specifically, to a preferred construction and a method for achieving that construction.

BACKGROUND

As early as the 1930's, rotary dental instruments began to employ diamond abrasive to advantage over fluted cutter type instruments. With the emerging popularity of high speed turbine dental handpieces diamond instruments gained further advantage and widespread usage. While there had been some experimentation with brazing and other forms of bonding to bond diamond abrasives to rotary dental tool blanks, the overwhelming standard method was mechanical entrapment in a layer of electroplate. This process usually employed nickel but frequently included nickel in combination with other metals, such as an overplate of chromium. In 1971, Lowder, et al. discovered advantages of a hard nickel braze bond composition, described in U.S. Pat. Nos. 3,894,673 and 4,018,576. The advantages of this composition manifested themselves in a dental tool manufactured by Abrasive Technologies, Inc., presently of Lewis Center, Ohio, and sold under the trademark TWO STRIPER™. The improvements incorporated into this new product spurred competition, resulting in improvements in electroplated diamond rotary instruments worldwide.

Throughout the industry, the principal attributes for diamond bonded dental tools are generally considered to be cutting speed and durability. In an attempt to sidestep the issue of durability, some manufacturers began to provide a "disposable" dental tool having an initial fast cutting speed with a competitive cost-per-use basis and the convenience of disposability. However, many early disposable tools were of inferior quality and exhibited accelerated dulling. Accordingly, the migration toward disposable diamond dental tools was initially slow to catch on, but has gained in popularity over the recent past.

Among the prior art products, the traditional offering was multiple choices of grit size to provide various tool characteristics. Coarse grit, typically in the range of 100-140 mesh was offered for rapid cutting, while fine grit in the range of 230-325 mesh was available for those practitioners who wanted to give a dental surface a finer finish in a second step. As diamond dental tools developed, in the 1980's and 1990's manufacturers began to boast of more diamond grit coverage on the cutting surface of the tools, many attempting to reach 100% concentration with coarser grits of up to 60 grit and improved diamond bonding. The emphasis on speed of cut and maintenance of the speed of cut after the first usage became the de facto standard by which dental tools were measured. This prompted a renewed interest in disposable tools, which had by this time improved in quality to the point they were seriously being considered as viable alternatives to the multiple-use tools.

To further increase cutting and durability performance in the tools of the prior art, manufacturers began to employ such methods as interrupting the dense, often approaching 100%, diamond grit surface area coverage. Examples of interrupted patterns included diamonds bonded in spiral or cross hatched patterns on the tool blank. This interruption in the gritted surface has the effect of forcing the leading grit crystals following the interruption to cut more effectively, even when they have dulled. Such a variety of a tool, also sold under the trademark TWO STRIPER™ TS2000 by Abrasive Technology, included a spiral pattern to compete with the ever growing popularity of coarser and, presumably, faster cutting tools. However, the use of a coarser grit on a diamond dental tool drives a need for a user to change tools in order to finish the work with a finer grit tool, thus requiring a separate, second step.

Even with the aforementioned improvements in initial cutting speed and durability, rotary diamond dental tools still suffer from a marked deterioration in cutting speed after multiple uses. What is needed is a dental tool that provides fast cutting using a finer grit, is durable and can reduce the overall amount of time the tooth is subjected to the abrasive actions of the tool. A dental tool that can be used for both cutting and finishing of dental material is also needed.

SUMMARY

A rotary diamond dental tool according to the present invention provides a fast cut using a finer grit, has improved durability over the tools available in the art and can eliminate the need for finishing operations by conducting both coarse and finishing operations with a single tool. The present invention results in an improved rotary dental diamond instrument construction.

After fabricating a dental blank, a head portion of the blank is rotated into and out of an adhesive, leaving a thin tacky film. Next, the head is rotated into and out of a cascade of diamond grit with a controlled rate of insertion/extraction and rotation to give a predetermined coverage, or percentage concentration, of diamond grit having a predetermined grit size. Next, the head is rotated into and out of a cascade of brazing powder having a predetermined particle size, at a controlled rate of insertion/extraction and rotation to give full coverage of the surfaces of exposed blank between the diamond crystals. Once the thin adhesive film is populated with diamond grit and braze particles, the tool is subjected to a fusing process. Fusing of the assembly is accomplished at the appropriate temperature and in a suitable atmosphere for the braze composition.

An aspect of the present invention is a rotary dental tool. The tool comprises a blank having a shaft portion and a head portion. A layer of adhesive substantially coats the head portion. A substantially single layer of grit comprising diamond crystals is embedded in, and extends from, the adhesive to a substantially uniform height, said grit covering a predetermined proportion of the surface area of the head portion. A bonding material substantially surrounds the diamond crystals, forming micro-channels between the diamond crystals. The micro-channels aid to cool the dental tool and facilitate debris removal.

Another aspect of the present invention is a method for producing a rotary dental tool, comprising the steps of selecting a blank having a shaft portion and a head portion; applying a thin layer of adhesive to substantially coat the head portion, the adhesive layer being thin enough that only a single layer of grit is deposited into the adhesive layer, the grit comprising diamond crystals embedded in, and extending from, the adhesive to a substantially uniform height, said grit covering a predetermined proportion of the surface area of the head portion, and substantially surrounding the diamond crystals with a bonding material, forming micro-channels between the diamond crystals. The micro-channels are believed to facilitate both the cooling of the dental tool during use and debris removal during cutting operations.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

1. Dental Tool

Figure 1:
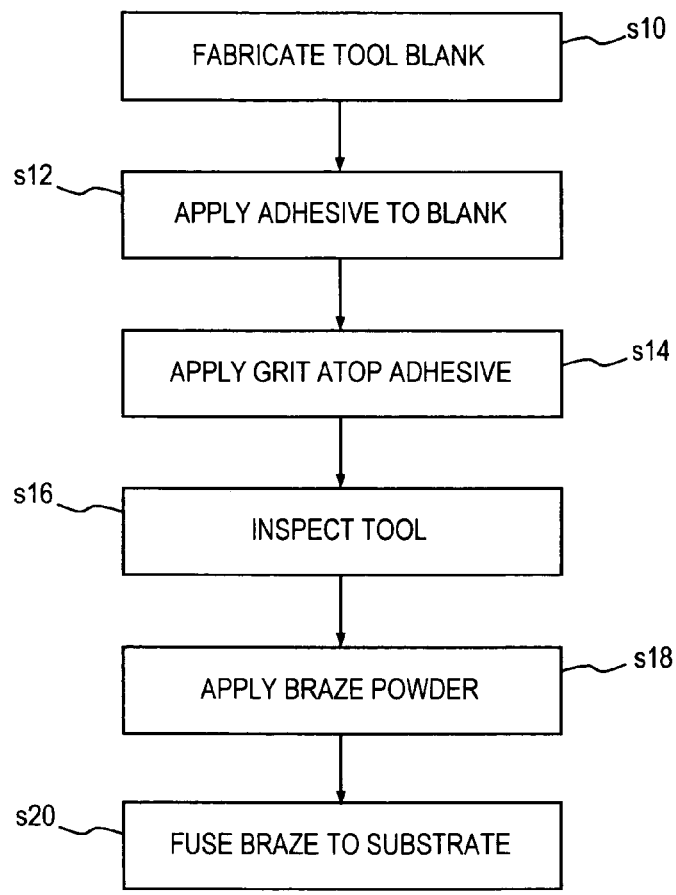
FIG. 1 is a flow diagram outlining a process for producing a rotary diamond dental tool according to an embodiment of the present invention.

A process for fabricating a rotary dental tool according to an embodiment of the present invention is shown in FIG. 1. At step s10 a substrate such as a dental rotary blank is fabricated. An example rotary blank 100, depicted in FIG. 2, comprises a shaft portion 102 and a head portion 104 of a select geometry. Shaft 102 is generally cylindrical and may be configured to couple to any conventional dental tool, such as a low-or high-speed air turbine dental handpiece. Head 104 is likewise generally conical, with particular dimensions, shapes and tapers being determinable for dental tools tailored for various dental procedures. Accordingly, the dimensions of a particular embodiment of shaft 102 and head 104 are left to the artisan. Blanks 100 may be machined in any conventional manner, such as with an automatic screw machine, or may be cast. Any suitable material may be selected for blank 100, including stainless steel, such as Carpenter 416. Although hardenable stainless steel is a preferred material for the blanks, other durable metals may be employed as well. In other embodiments blank 100 may be a non metallic material including, without limitation, plastic, composite and ceramic materials, coupled with suitable bonding methods.

Figure 2:
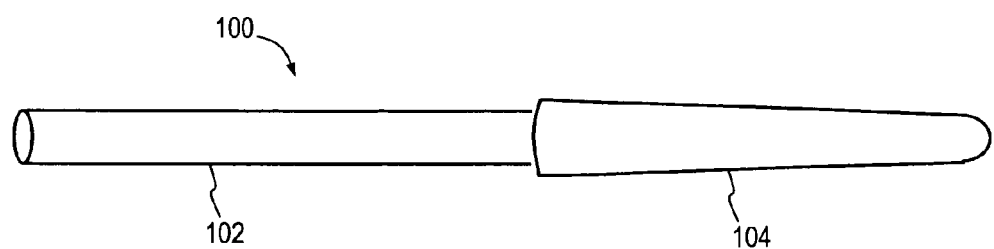
FIG. 2 depicts a dental blank according to an embodiment of the present invention.

With continued reference to FIGS. 1 and 2, head 104 is coated with a suitable adhesive material, preferably an adhesive film, at step s12. In one embodiment head 104 is coated by rotating blank 100 about shaft 102 and confronting the surface of a pool of adhesive material by the head, the thickness of the film being generally proportional to the viscosity of the adhesive, shaft 102 rotation speed and the depth of penetration into the surface of the adhesive by the head. There are any number of conventional adhesive films suitable for the bonding means for of the dental tool that may be selected, including epoxy. A thin film of adhesive is preferred to avoid the piling up of multiple layers of diamond crystals and braze particles, which are applied in subsequent steps and discussed below. A thin film for purposes of the instant invention is the thickness that is effective to retain no more than a single layer of diamond grit and braze powder. Thus, for a given concentration of diamond grit the required bonding level is determined by the ratio of sizes between the diamond crystals and the braze particles.

At step s14 a diamond grit is applied to the adhesive-coated head 104 of blank 100, to a predetermined surface-area coverage, or percentage concentration, of diamond grit having a predetermined grit size. In one embodiment head 104 is coated by rotating blank 100 about shaft 102 and passing the head through a cascade or screen of diamond grit. The cascade of grit may be produced in any conventional manner, such as with a vibratory feeder like that manufactured by FMC Syntron. The amount of coverage of grit, i.e., percentage of the surface area coverage, on head 104 is generally proportional to the concentration of the grit in the cascade and the amount of time the head is exposed to the cascade. This is generally controlled by the insertion/extraction rate and the rate of rotation of the blank through the cascading diamond grit. In the present invention the diamond grit preferably comprises particles of a substantially uniform size, ranging from around 80-230 mesh and having an aspect ratio of grit particles less than about 1.4, the aspect ratio equaling the ratio of the maximum to minimum average dimensions of the particle.

In producing tools according to the present invention whereby the blank is coated with a thin layer of adhesive and a reduced concentration of diamond, it was observed that diamond crystals tend to bond with the minimum dimension vertical to the blank surface. It is believed that they rotate to the broadest contact surface due to surface tension of the adhesive and thus produce a more uniform cutting surface for a given grit size than a full concentration would provide based on a given aspect ratio for a grit size.

At step s16 the grit-coated blank 100 may optionally be inspected to ensure that the percentage of coverage and uniformity are within the desired parameters, preferably less than 65%, although some embodiments may have concentrations that approach about 90%. Some embodiments may have multiple or variable concentrations on different regions of the head. Inspection may be performed upon each blank 100 or a statistically-derived sampling, and may be performed visually by human inspectors and/or using machine-vision techniques now known or developed in the future.

At step s18 braze particles are applied to the adhesive and grit-coated head 104 of blank 100. In one embodiment head 104 is coated by rotating blank 100 about shaft 102 and passing the head through a cascade or screen of braze powder. The cascade of powder may be produced in any conventional manner, such as with a vibratory feeder. The amount of coverage of braze powder in the available spaces between diamond grit, i.e., percentage of the surface area coverage, on head 104, is preferably 100% in a single layer, achieved by the amount of time the head is exposed to the cascade and the density of the cascade. The head 104 is rotated into and out of a cascade of brazing powder having a predetermined size, at a controlled rate of insertion/extraction and rotation to give full coverage of the surfaces of exposed blank between the diamond crystals. In one embodiment of the present invention a braze alloy comprising a spherical powder of the Ni—Cr—B family may be used. This alloy is sold under the trademark LM NICROBRAZ™ by Wall Colmonoy, among others.

In some embodiments of the present invention the braze particles are substantially spherical. In other embodiments the braze bonding material may be selected to have a mesh size that is substantially the same as the mesh size of the diamond grit. In still other embodiments the braze bonding material may have a mesh size that is one to five mesh sizes smaller than the mesh size of the diamond grit. In a preferred embodiment, the bonding level is controlled by applying single layers of diamond grit in a predetermined concentration with 100% coverage of braze particles of a predetermined size on the exposed blank surfaces between the diamond grit.

Figure 3:
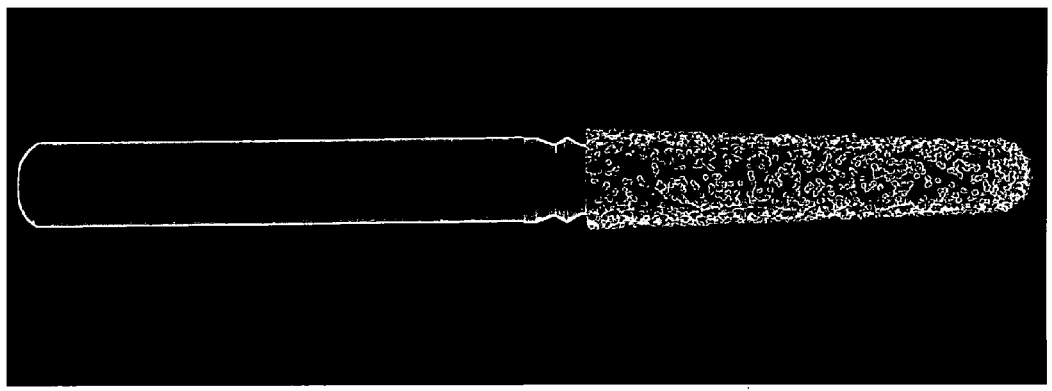
FIG. 3 is an SEM micrograph of a rotary dental tool according to an embodiment of the present invention.

At step s20 the braze powder applied to head 104 at step s18 is fused to melt the powder such that it substantially surrounds and captivates the diamond grit to the blank. In one embodiment of the present invention fusing of the assemblies is accomplished in a tube furnace with flowing hydrogen in the temperature range of about 1910° F. to 1960° F. A finished dental tool, shown in the scanning electron microscope (SEM) micrograph of FIG. 3, results after the completion of step s20 and the assembly has cooled. Although not required, the finished dental tool may optionally be heat treated by any conventional process after completion of step s20.

In other embodiments a conventional electroplate composition, bonding diamond crystals with nickel or other compositions, may be used in lieu of steps s12 through s20. Electroplating processes are well-known in the art and thus will not be reiterated here except to say that once the blank is patterned with a resist appropriate to avoid the plating chemistry, the blank can be immersed in a diamond bed and plating solution and treated in the same manner as if full coverage were the goal. Many varieties of resist exist which may be tailored to the plating chemistry and can be applied in a number of ways, such as by spraying or roll transfer to achieve a micro-channel pattern of the present invention. Upon removal from the bed, the plating process is continued until the desired level of plating is achieved. Afterwards, the resist is removed by the appropriate dissolution technique and a tool of the present invention is thus produced by an alternate bonding technique.

Similarly, another embodiment of this invention is practiced with one of the so-called "electroless" or chemical plating solution which deposits a bond of NiP or NiB alone or in combination with electroplating. However, in order to form the micro-channels to aid in the cutting efficiency of the dental tool, a predetermined surface of the tool head, e.g., around 35%, is covered with resist material in a random pattern. In this manner, the remaining 65% of the head will be subject to the electroplating process and deposition of diamond crystals in a concentration that approached that previously described in connection with the brazing process.

In still other embodiments bonding may be accomplished using a non-metallic material including, but not limited to, adhesives, potting, epoxy and ceramic. In yet other embodiments bonding may be accomplished using an active metal brazing material, as is well-known in the art.

Figure 4:
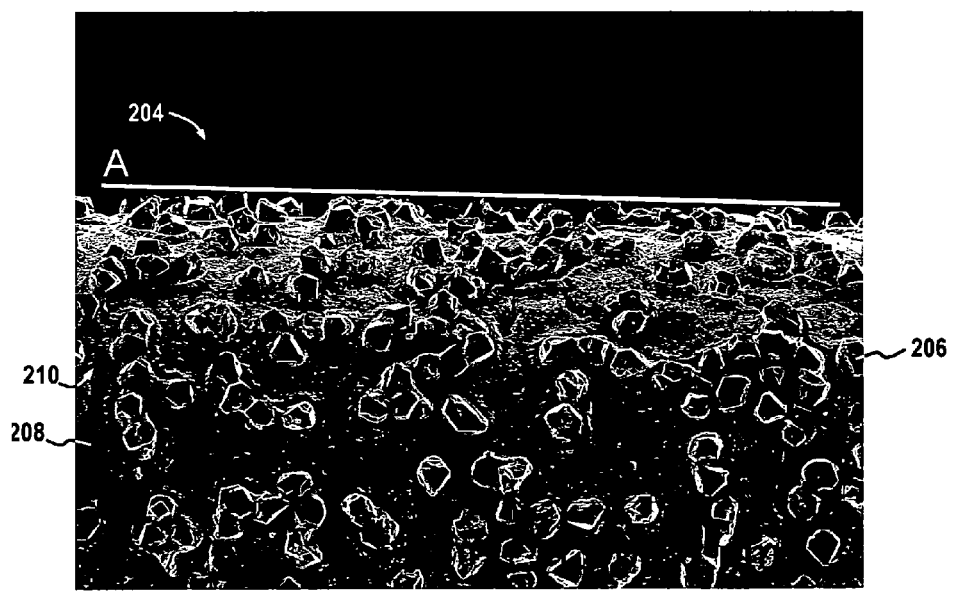
FIG. 4 is an SEM micrograph of a section of a rotary diamond dental tool according to the present invention having 170 mesh construction exhibiting substantial uniformity of crystal height.
Figure 5:
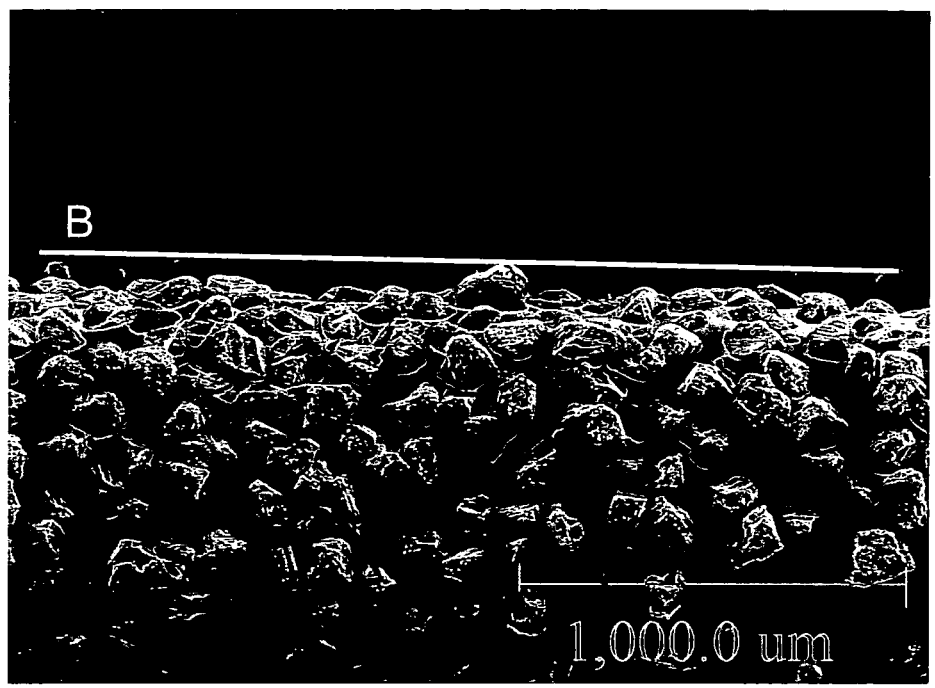
FIG. 5 is an SEM micrograph of a section of an 80 mesh coarse grit of the prior art electroplated diamond instrument showing non-uniformity of crystal height.
Figure 6:
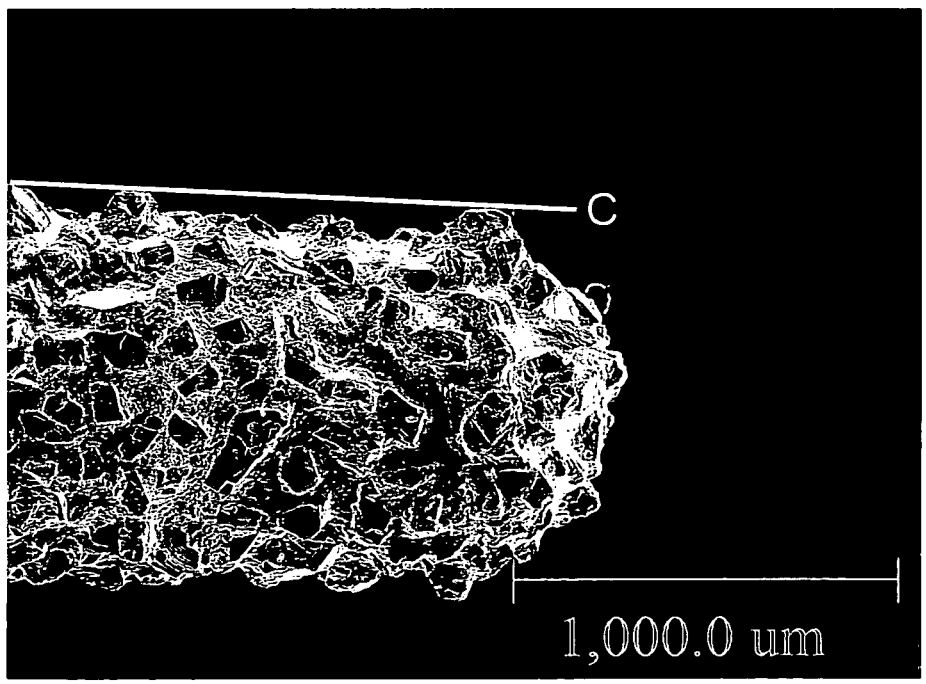
FIG. 6 is an SEM micrograph of the tip of a premium 120 mesh coarse grit brazed diamond instrument also of the prior art likewise illustrating non-uniformity of crystal height.
Figure 7:
FIG. 7 is an SEM micrograph of a section of a coarse grit electroplated instrument of the prior art in which a spiral pattern has been incorporated by a masking technique to allow the instrument to cut faster for a longer time than a standard instrument of the same grit size.
Figure 8:
FIG. 8 is an SEM micrograph of the finish achieved with a prior art dental tool.
Figure 9:
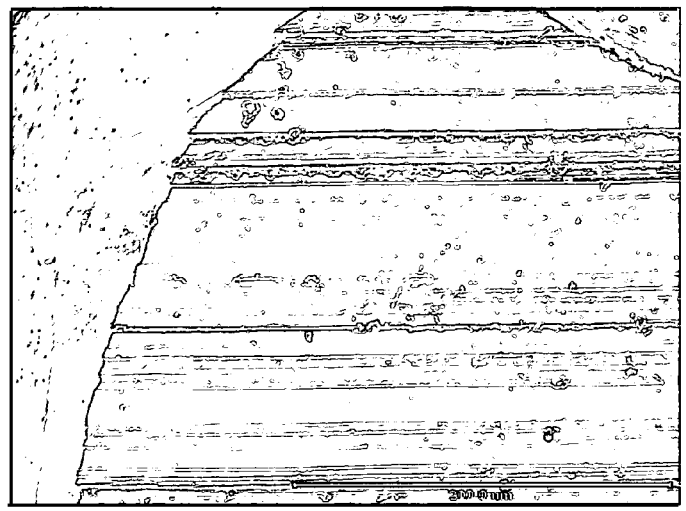
FIG. 9 is an SEM micrograph of the finish achieved with a dental tool according to an embodiment of the present invention.
Figure 11:
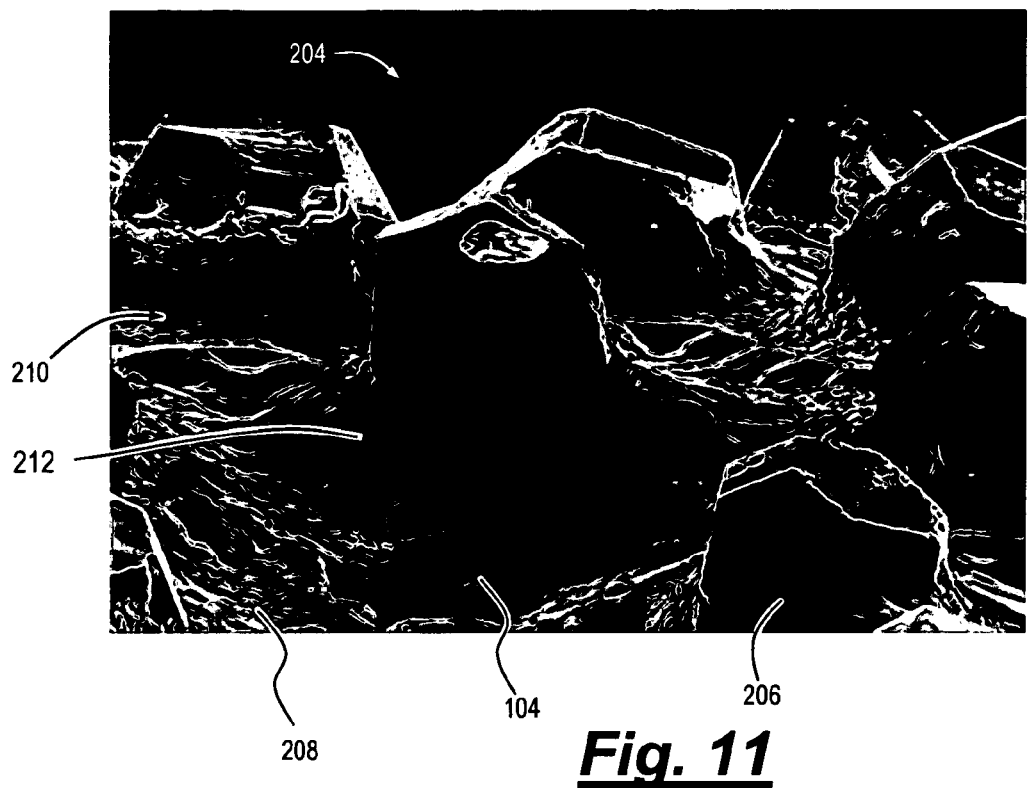
FIG. 11 is an expanded fragmentary view of the SEM micrograph of FIG. 4.
Figure 12:
FIG. 12 is an expanded fragmentary view of the SEM micrograph of FIG. 6.

In a preferred embodiment of the present invention a diamond dental instrument produced by the process of FIG. 1 has a finer, and relatively uniform sized grit ranging between 170-200 mesh and having lower concentration or coverage of diamond than coarser-grit, heavier coverage prior art tools. In one embodiment the concentration, of diamond grit is a single layer of non-pyramidal-shaped diamond crystals in the range of about 35-65% surface area coverage, with bonding principally only immediately around the bases of the crystals which are themselves relatively uniform in size with a small aspect ratio (see FIGS. 4 and 11). These crystals are first placed onto the head of the blank with less than 90% surface area coverage. This coverage allows the requisite space to dispose the crystals in a single layer extending uniformly in height from the head of the blank (see FIGS. 4 and 11). Contrasted with this, prior art tools (see FIGS. 5 and 6) have higher density diamond grit coverage. As can be seen, this leads to diamonds not all being disposed in a single layer and having non-uniform diamond crystal heights. In this embodiment the diamond crystals are randomly arranged as singles and small clusters and having interconnected void spaces between adjacent crystals and clusters that form continuous micro-channels. As can be seen in FIGS. 4 and 11, these micro-channels extend proximate the surface of the blank with a thin film of braze coating the head of the blank between the diamonds and a thin film of braze coating a minor portion of the sides of the diamond crystals proximate the surface of the blank. The micro-channels aid to cool the dental tool and facilitate debris removal. An example rotary dental tool 200 produced using the process of FIG. 1 is shown in the SEM micrograph depicted in FIG. 3, the dental tool comprising a shaft portion 202 and a cutting head 204. An expanded view of a cutting head 204 according to an embodiment of the present invention is shown in the SEM micrograph of FIG. 4 and the expanded view of this micrograph in FIG. 11. As can be seen, a single layer of individual diamond crystals 206 and clusters of said diamond crystals are spaced apart from one another. In addition, the profile of the diamond crystals 206 is relatively uniform in height above the surface of the blank with few particles protruding above the others, as illustrated by construction line "A" in FIG. 4. This is in contrast to the prior art dental tools of FIGS. 5, 6 and 12, wherein construction lines "B" and "C" in FIGS. 5 and 6 respectively illustrate the lack of uniformity of crystal height in a given plane. The degree of diamond crystal 206 height deviation seen in FIGS. 5, 6, and 12 is sufficient to cause profound differences in cutting performance as seen in FIGS. 8 (prior art) and 9 (present invention). Furthermore, a bonding material 208 captivating the diamond crystals 206 is generally limited to immediately surrounding only those portions of the diamond crystals proximate the surface of the blank, thereby forming interconnected void spaces 210 between the spaced apart individual diamond crystals and clusters of diamond crystals. The interconnected void spaces 210 extend to the surface 104 of cutting head 204 (FIG. 11), with a thin film of bonding material 208 on the head and a thin film of bonding material on a minor portion of the sides of the diamond crystals 206, leaving a major portion of the diamond crystals free of bonding material and available for cutting. A fillet 212 of bonding material is around the bases of the diamond crystals 206 with a thin film of braze material rising partially upward along the sides of the diamond crystals and also flowing partially over the surface 104 of cutting head 204. Interconnected void spaces 210 aid to cool and retard dulling of diamond crystals 206 by facilitating lubrication around the crystals. These features result in a cutting head 204 that cuts faster and lasts longer than the relatively coarse grit diamond tools of the prior art (see, e.g., FIGS. 5-7), typically 120 mesh or coarser. Tools produced according to the present invention also provide a finish that is not only smoother than the coarser instruments but nearly that of prior art finer grit instruments. This phenomenon is related to uniformity of crystal 206 height (FIG. 4) causing more crystals to be uniformly engaged with the work surface and lacking the unevenly protruding crystals of the prior art (FIGS. 5 and 6) that non-uniformly cut the work surface. Comparative SEM micrographs of a tooth surface finish cut made with a prior art tool and a tool according to an embodiment of the present invention are shown in FIGS. 8 and 9, respectively.

In both electroplating and brazing bonding processes with full concentrations of diamond according to the prior art, there is a tendency to bond some crystals securely at a height significantly above the average crystal size (see, e.g., FIGS. 5 and 6). These protruding crystals are the first to confront the tooth surface and end up doing most of the cutting but, as a result, dull rapidly. Once dulling begins on these relatively few protruding crystals, the tool slows markedly in cutting rate and has a less smooth feel because it is not cutting as easily. In contrast, using the present invention (see FIG. 4), the lesser coverage and smaller mesh size of diamond crystals actually allows many more crystals to contact the tooth structure. With more crystals engaged, dulling occurs more slowly and so the dental tool of the present invention initially cuts faster and lasts longer.

While the dental tool according to the present invention may be produced using a single unique brazing process, it is believed that the same advantages may be achieved using other processes, both conventional and otherwise. For example, in another embodiment, blank 100 is first coated with a random resist coating in the pattern of the microchannels of the present invention and then diamond bonded in the remaining spaces by electroplating. As a result, the electroplate bonding only occurs in areas absent of the resist coating and, after removal of the resist, yields a similar pattern according to the previously described embodiment.

In one embodiment of the present invention at least one of the size, proportion of coverage and arrangement of diamond crystals may be selected to facilitate a dental tool that is capable of both removal of stock and finishing of dental material.

In another embodiment of the present invention the size, bond height, arrangement and concentration of diamond crystals may be optimized for the size and shape of tool, including varying diamond crystal concentration from one region to another of the head portion.

2. Test Data

Tools produced in accordance with the present invention were evaluated using plunge cuts in tooth enamel. These evaluations have demonstrated that tools produced according to the present invention cut smoother and more rapidly at a suitable load in comparison to tools of the prior art having the same geometry but utilizing coarser grit. Some of the prior art tools actually stalled the hand piece under identical loading conditions. These tests clearly demonstrate that a dental tool according to the present invention cuts at a faster rate, while using a finer grit than coarser tools available in the art.

Figure 10:
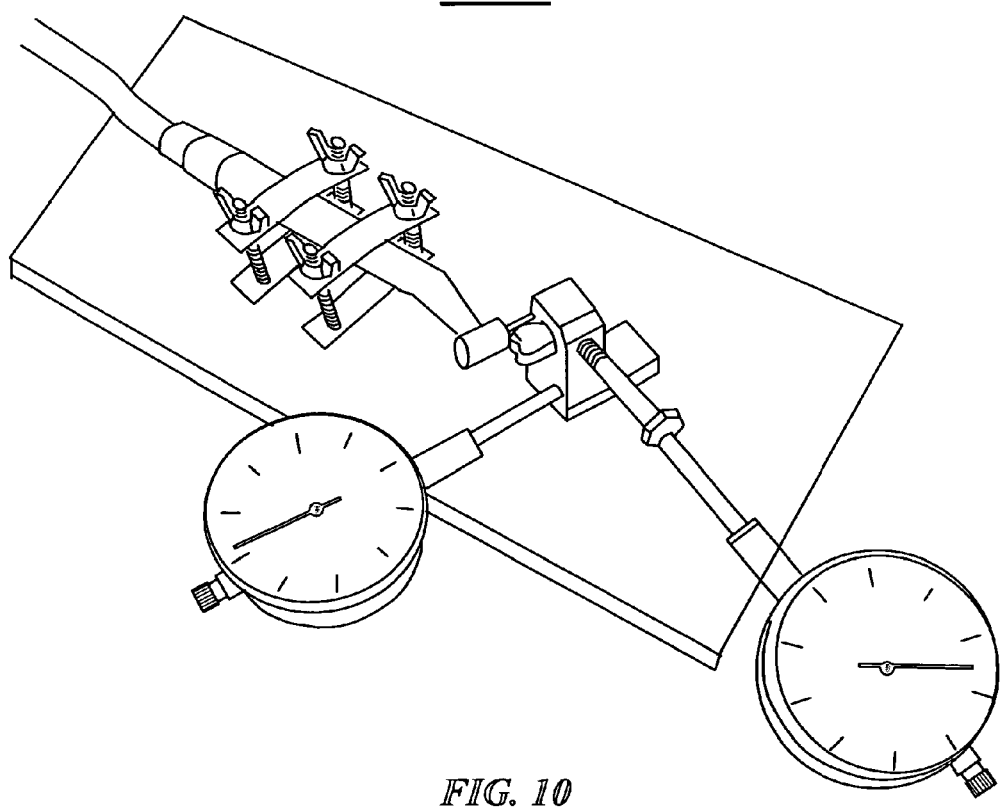
FIG. 10 is a view of a cutting evaluation apparatus showing a mounted extracted molar, depth gage, handpiece, diamond instrument and means for measuring an applied load.

It is desirable to consider various combinations of grit size, concentration and bond height and test the cutting efficiency. Accordingly, testing has been performed upon tooth structure by mounting extracted test molars in a conventional potting material for easy gripping and orientation in a test apparatus, such as the apparatus of FIG. 10. Plunge cutting comparison tests can be performed side by side in the same test tooth while opposite sides or alternate sections can be used for comparative tests in the more typical usage of reduction of the enamel surface in crown preparation. Using the apparatus depicted in FIG. 10 it is possible to perform the same cutting operation in the laboratory as a dentist performs in the oral cavity, but with the advantage of being able to quantify the results. For example, a plunge cut with a tapered instrument horizontal to the buccal surface of an extracted and mounted molar allow a side-by-side comparisons of the results of different tools of the same size and shape. It is possible to evaluate initial cutting rate, deterioration of the cutting rate and life on a comparative basis by alternating instruments in the same handpiece, performing the same operation on adjacent portions of the same teeth. Realistic loads, i.e., cutting forces, are readily determined by surveying dental practitioners, i.e., having them perform an operation on a tooth mounted on a scale.

In a survey of dentists using prior art tools the reported average of the number of full crown "preps" was just over 6, while the average number of crown preps using tools produced in accordance with the present invention, was over 8. This represents an improvement in durability of roughly 33%. Over 90% of these same dentists indicated that they would prefer a dental tool produced according to an embodiment of the present invention over prior art dental tools. For example, one practitioner has reported usages of a round-end tapered design in 8 mm length of 20, 22 and 25 crown preps and that instruments produced according to the present invention cut faster than the extra coarse, 80 mesh, disposable tool that he had been using.

During development of the present invention it was discovered that the most effective cutting for an 8 mm round end taper was achieved by a heretofore unknown combination of parameters, i.e., medium grit, e.g., about 120-270 mesh, preferably about 170-200 mesh, about 40-50% diamond coverage, with high bond adjacent to the crystals, with little to no bond in the spaces between. This construction combination was subsequently applied to 21 additional shapes, which are popularly used for rapid removal of tooth structure and found excellent performance results. These are commonly referred to as crown and bridge operations. Five of these tool shapes were offered for comparisons in the aforementioned survey in which the practitioner was asked to compare only those shapes to those same shapes of prior art tools with which he was familiar with. All five tool shapes received excellent reports as compared to the corresponding prior art tools.

3. Conclusion

It is believed that the use of tools according to the present invention in the preparation of teeth for crowns represents a significant improvement in preserving vital tooth health resulting from reduced heat and mechanical trauma on the tooth. "Micro channels," or interconnected spaces between diamond crystals and crystal groupings or clusters, appear to be very effective in cooling the diamonds and retarding dulling from overheating and a lack of lubrication. This reduced heat is believed to be beneficial to the preservation of tooth vitality.

While certain preferred embodiments of the present invention have been disclosed in detail, it is to be understood that various modifications may be adopted without departing from the spirit of the invention or scope of the following claims. For example, variations in grit size as well as concentration may be selected to optimize the performance of the different shapes and sizes of dental diamond rotary instruments, of which there are many.

What is claimed is:

1. A dental rotary tool comprising:
   a blank having a shaft portion and a head portion;
   a single layer of grit disposed upon the blank, the grit comprising at least one of spaced apart individual diamond crystals and spaced apart clusters of diamond crystals, the diamond crystals each having a base and extending to a generally uniform height above the surface of the blank, said grit covering less than about 90% of the surface area of the head portion; and
   a bonding material comprising a braze composition that is generally limited to a fillet surrounding only the bases of the diamond crystals at the surface of the blank, thereby forming interconnected void spaces on the blank between the diamond crystals, the interconnected void spaces providing continuous micro-channels for cooling the diamond crystals and removing debris, the micro-channels extending to the surface of the head portion, said head portion having a thin film of braze bonding material and a thin film of braze bonding material on a portion of the sides of the diamond crystals, the braze bonding material durably captivating the diamond crystals to the blank while leaving a major portion of the diamond crystals free of braze bonding material and available for cutting.

2. The dental tool of claim 1 in which the diamond crystal size is generally uniform in a select size, the select size ranging between about 120 to 270 mesh.

3. The dental tool of claim 1 wherein the shaft portion of the blank is configured to couple to a high-speed air turbine dental handpiece.

4. The dental tool of claim 1 wherein the blank comprises hardenable steel.

5. The dental tool of claim 1 wherein at least one of the size, proportion of coverage and arrangement of diamond crystals facilitate both removal of stock and finishing of dental material.

6. The dental tool of claim 1 in which the concentration of diamond crystals is varied from one region to another of the head portion.

7. The rotary dental tool of claim 1 wherein the tool is effective to both rapidly reduce the structure of a tooth and finish a surface of the tooth.

8. The rotary dental tool of claim 1 wherein the diamond grit covers about 65 percent or less of the surface area of the head portion.

9. The rotary dental tool of claim 1 wherein the rotary dental tool is effective to preserve tooth vitality.

10. A dental rotary tool comprising:
    a blank having a shaft portion and a head portion;
    a single layer of grit disposed upon the blank, the grit comprising at least one of spaced apart individual diamond crystals and spaced apart clusters of diamond crystals, the diamond crystals of about 120 mesh or smaller, said diamond crystals each having a base and extending to a generally uniform height above the surface of the blank, said grit being randomly distributed over the head portion and covering less than about 90% of the surface area of the head portion; and
    a bonding material comprising a braze composition that is generally limited to a fillet surrounding only the bases of the diamond crystals at the surface of the blank, thereby forming interconnected void spaces on the blank between the diamond crystals, the interconnected void spaces providing continuous micro-channels for cooling the diamond crystals and removing debris, the micro-channels extending to the surface of the head portion, said head portion having a thin film of braze bonding material and a thin film of braze bonding material on a portion of the sides of the diamond crystals, the braze bonding material durably captivating the diamond crystals to the blank while leaving a major portion of the diamond crystals free of braze bonding material and available for cutting.

11. The dental tool of claim 10 wherein the shaft is configured to couple to at least one of a high and low speed dental handpiece.

12. The dental tool of claim 10 in which the blank comprises hardenable steel.

13. The dental tool of claim 10 in which the blank is non-metallic.

14. A method for producing a rotary dental tool, comprising the steps of:
    selecting a blank having a shaft portion and a head portion;
    selecting a grit comprising diamond crystals;
    selecting a braze composition comprising braze particles;
    coating the head portion with a layer of adhesive sufficient to capture only a single layer of grit and particles;
    depositing a single layer of grit into the adhesive layer, the grit comprising at least one of spaced apart individual diamond crystals and spaced apart clusters of diamond crystals, the diamond crystals each having a base and extending to a generally uniform height above the surface of the blank, said grit covering a predetermined proportion of the surface area of the head portion;
    surrounding the diamond crystals with a layer of braze particles of such size and amount to achieve a suitable braze bonding level for a given size and concentration of diamond grit; and
    fusing said assembly in a furnace, thereby bonding the braze particles and the diamond crystals such that a fillet of braze surrounds only the bases of the diamond crystals at the surface of the blank, thereby forming interconnected void spaces on the blank between the diamond crystals, the interconnected void spaces providing continuous micro-channels for cooling the diamond crystals and removing debris, the micro-channels extending to the surface of the head portion, said head portion having a thin film of braze bonding material and a thin film of braze bonding material on a portion of the sides of the diamond crystals, the braze bonding material durably captivating the diamond crystals to the blank while leaving a major portion of the diamond crystals free of braze bonding material and available for cutting.

15. The method of claim 14, further comprising the step of arranging the diamond grit to cover about 65 percent or less of the surface area of the head portion.

16. The method of claim 14 further comprising the step of selecting diamond grit having a substantially uniform particle size.

17. The method of claim 14, further comprising the step of selecting a braze bonding material having a mesh size substantially same as the mesh size of the diamond grit.

18. The method of claim 14, further comprising the step of selecting a braze bonding material having a mesh size from one to five mesh sizes smaller than the mesh size of the diamond grit to control bond depth.

19. The method of claim 14, further comprising the step of simultaneously hardening the steel blank when fusing the assembly.

20. The method of claim 14, further comprising the step of additional heat treatment of the dental tool after the bonding step.

* * * * *